Figure 1:
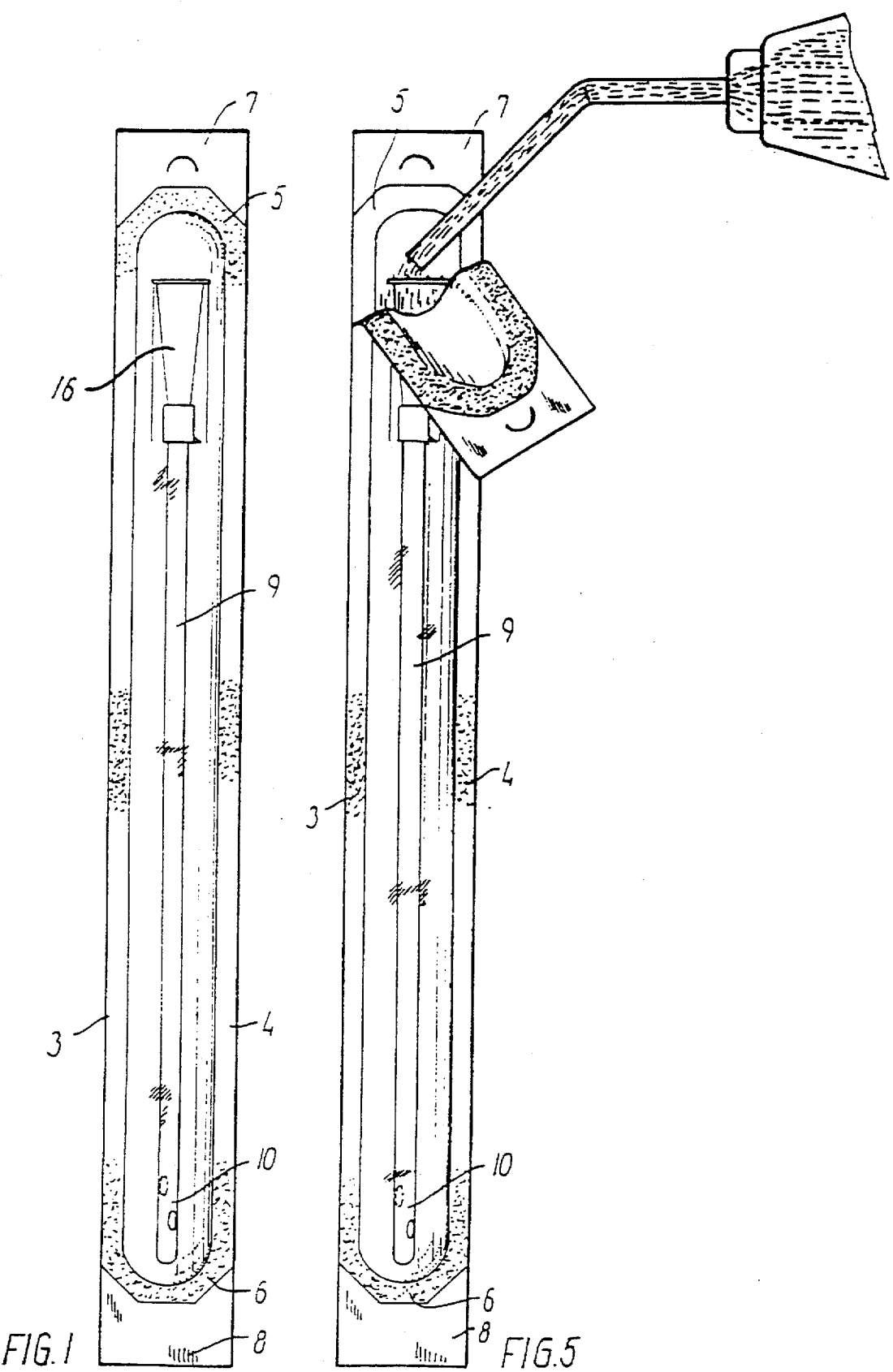

United States Patent [19]

Rødsten

[11] Patent Number: 5,895,374

[45] Date of Patent: Apr. 20, 1999

[54] APPLICATOR AND METHOD FOR USE IN NON-CONTAMINATING APPLICATION OF A MEDICAL CATHETER

[75] Inventor: Carsten Bob Rødsten, Kirke-Hyllinge, Denmark

[73] Assignee: Coloplast A/S, Denmark

[21] Appl. No.: 08/930,420

[22] PCT Filed: Mar. 29, 1996

[86] PCT No.: PCT/DK96/00130

§ 371 Date: Sep. 29, 1997

§ 102(e) Date: Sep. 29, 1997

[87] PCT Pub. No.: WO96/30277

PCT Pub. Date: Oct. 3, 1996

[30] Foreign Application Priority Data

Mar. 29, 1995 [DK] Denmark .................. 0330/95

[51] Int. Cl.$^6$ .................. A61M 5/00

[52] U.S. Cl. .................. 604/163; 604/171; 206/364

[58] Field of Search .................. 604/171, 163, 604/263; 206/364, 370

[56] References Cited

U.S. PATENT DOCUMENTS

| 3,035,691 | 5/1962 | Rasmussen et al. . | |
|---|---|---|---|
| 3,112,031 | 11/1963 | Stewart | 604/171 |
| 3,934,721 | 1/1976 | Juster et al. | 206/364 |
| 3,967,728 | 7/1976 | Gordon et al. . | |
| 4,230,115 | 10/1980 | Walz, Jr. et al. | 604/171 |
| 4,906,237 | 3/1990 | Johansson et al. . | |
| 4,925,448 | 5/1990 | Bazaral | 206/364 X |

FOREIGN PATENT DOCUMENTS

| 0613697 | 9/1994 | European Pat. Off. . |
| 2676038 | 4/1991 | France . |
| 1498356 | 1/1978 | United Kingdom . |
| 9416747 | 8/1994 | WIPO . |

*Primary Examiner*—John D. Yasko
*Attorney, Agent, or Firm*—Ostrolenk, Faber, Gerb & Soffen, LLP

[57] ABSTRACT

A non-contaminating application of a medical catheter into a body canal, in particular a urethra catheter, and of the kind provided with a friction-reducing surface coating, is effected by placing the catheter in a packaging designed as an applicator and composed of two essentially rectangular plastic foil blanks which are joined in essentially linear peeling zones extending along their edges, the catheter being placed with its distal insertion end positioned opposite a predetermined first zone of the edge joint. By the application, the walls are separated gradually and completely in peeling zones in the direction away from the first zone during simultaneous insertion of the catheter.

12 Claims, 3 Drawing Sheets

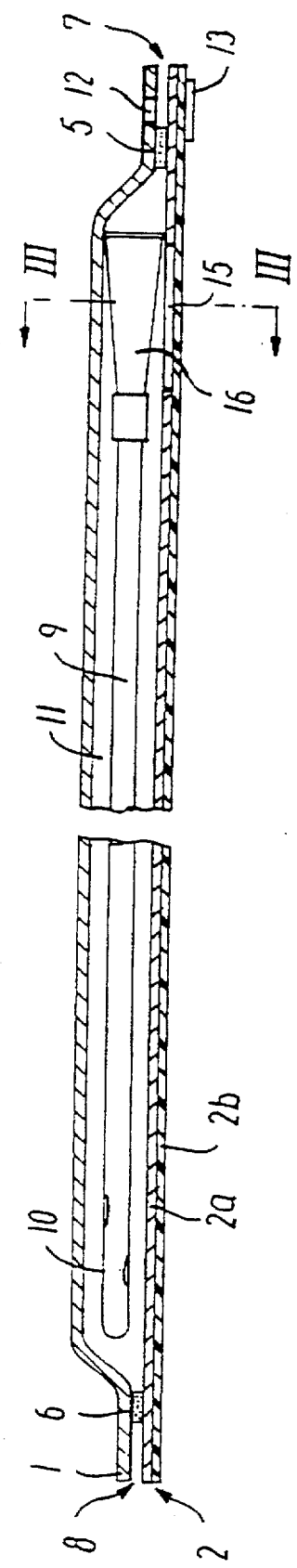
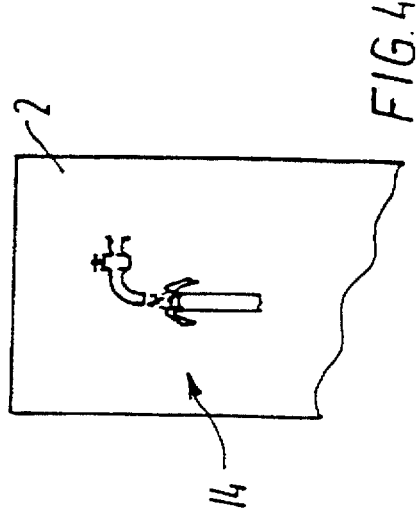
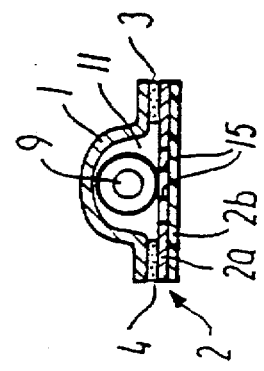
FIG. 2
FIG. 3
FIG. 4

APPLICATOR AND METHOD FOR USE IN NON-CONTAMINATING APPLICATION OF A MEDICAL CATHETER

The invention relates to an applicator for use in non-contaminating application of a medical catheter for insertion into a body canal, in particular a urethra catheter, and of the kind provided with a friction-reducing surface coating.

French Utility Certificate No. 2 676 038 discloses a plastic foil packaging for use with acupuncture and injection needles, swab sticks and similar medical utensils, designed as an elongated sheath of two plastic foil blanks which along their side and end edges are joined in such a way that in upper and lower sections of the sheath, peeling zones are provided for relatively easy separation of the plastic foil blanks, whereas a strong adhesion between the two plastic foil blanks is provided in a central area.

When using this known packaging for an acupuncture or injection needle, the needle is Positioned in the packaging with an enlarged head portion in the upper section of the sheath and the pointed end in the lower section. By the operating manipulation, the operator grips the central part of the sheath where the two foils are fastened strongly to each other. By separation of the foil blanks in the upper section, access is thus provided to the head portion of the needle with a view to manipulating an acupuncture needle or to coupling an injection needle with a syringe. The application and the location of an acupuncture or injection needle at the acupuncture or injection area are effected by separation of the foil walls in the lower section without touching the part of the needle positioned in this section. It is an essential feature of this known packaging and application design that during insertion of the needle, the packaging stays connected to this.

On the basis of this known technique, it is the object of the invention to provide an applicator of the stated kind by which a medical catheter can be applied, ie. inserted into a body canal, with no risk of contamination and at the same time, the catheter is separated completely from the packaging.

Therefore, the applicator according to the invention is characterized in that it is designed as a packaging composed of two essentially rectangular edge-joined foil blanks forming the walls for a space in which the catheter may be positioned with its distal insertion end opposite a predetermined first zone of the edge joint, and that the edge joint extending along all side edges of these foil walls is composed of essentially linear peeling zones permitting complete separation of the two foil walls with a view to contamination-free application of the catheter through gradual, complete separation of the foil walls in said peeling zones in the direction away from said first zone by a pull essentially perpendicular to the longitudinal direction of the catheter and during simultaneous insertion of the catheter into said body canal without touching the catheter.

By this applicator there is achieved a safe application of the catheter both when the catheterization is effected by nursing staff or by the patient himself as the catheter can be controlled in a precise manner during the insertion merely by gripping the foil walls at the said first zone, and the insertion force is provided by the pull in the foil walls exerted during the gradual separation hereof in the direction away from the first zone. The insertion can thus be made in a simple way without touching the very catheter and without consequent contamination, whereby the infection risk is reduced.

In order to help the user to help himself as much as possible, the applicator can, when used in connection with catheters of the kind where the friction-reducing surface coating is activated by moistening with water immediately before the application, according to an advantageous further development of the invention, be provided with instructions for initial separation of local parts of the two walls merely at said first zone or a remote second zone of the edge joint in order to permit preparation of the catheter by introduction and removal of a moistening medium through the thus formed aperture prior to the application of the catheter.

Such catheters are well known per se, among others from EP-B-0217771 and WO 94/16747.

The moistening medium is preferably water, isotonic salt water or alike.

An appropriate embodiment of the applicator is according the invention characterized in that said foil blanks are elongated and adapted to the form of the catheter such that they envelop the catheter relatively closely, said first and second zones being situated at opposite ends of the thus formed elongated sheath.

In order to ease the use of the applicator further, there may at said opposite ends outside said first and second zones be provided non-joined end portions of the foil walls.

A particularly appropriate embodiment of the applicator is achieved according to the invention in that the foil walls comprise a front wall and a rear wall of which the First is a transparent single-layer plastic foil whereas the second comprises a laminate composed of a plastic foil layer joined with the front wall and a back layer joined with the opposite side of the plastic foil layer.

With a view to sterilization of the catheter upon its positioning in the applicator serving as packaging, this back layer may be of gas-permeable paper, and in the plastic foil layer of the rear wall within the edge joint, there may be designed at least one aperture for use with gas sterilization of the catheter upon its positioning in the edge-joined packaging.

In order to avoid contact between the paper back layer and the catheter, this aperture is preferably situated in the proximity of said second zone of the edge joint.

By application of the catheter it is practical if the applicator may hang independently while the patient is made ready, and by catheters of the kind where the friction-reducing surface coating is activated by moistening, the necessary preparation is made during which the surface coating swells. For this purpose, a user-friendly design of the applicator is achieved by providing it with a hanging device, eg. in the form of a hole in the front wall of the applicator and/or an adhesive tape with a protective coating positioned on the back layer. By designing the applicator with both forms of hanging devices, a considerable flexibility is obtained for the user as to choice of hanging place.

The invention further relates to a method for manufacture of a combination of an applicator as indicated above and a medical catheter for insertion into a body canal, in particular a urethra catheter, and of the kind provided with a friction-reducing surface coating.

According to the invention, this method is characterized in that the applicator is designed as a packaging composed of two essentially rectangular, edge-joined foil blanks which are joined in essentially linear peeling zones extending along their edges, and that the catheter is positioned in the applicator with its distal insertion end opposite a predetermined first zone of the edge joint.

As a further characteristic feature of this method, the catheter may be sterilized upon positioning in the applicator and closure of the edge joint.

Such a sterilization may be effected either by radiation sterilization or in an appropriate way whereby one foil blank serving as rear wall for the applicator is designed as a laminate of an internal single-layer plastic foil and an external back layer of gas-permeable paper, and the sterilization is carried out as a gas-sterilization through said back layer and at least one aperture in said single-layer plastic foil.

Finally, the invention relates to a method of non-contaminating application of a medical catheter for insertion into a body canal, in particular a urethra catheter and of the kind provided with a friction-reducing surface coating, by using an applicator as indicated above.

This method is according to invention characterized in that non-contaminating application of the catheter is effected through gradual, complete separation of the walls of the applicator in said peeling zones in the direction away form said first zone by a pull essentially perpendicular to the longitudinal direction of the catheter and during simultaneous insertion of the catheter into said body canal without touching the catheter.

When using this method for application of a catheter of the kind where the friction-reducing surface coating is activated by moistening, there is prior to said application effected a preparation of the catheter by initial separation of local parts of the foil walls merely at said first zone or a remote second zone of the edge joint and by introduction and removal of a moistening medium through the thus provided aperture.

Figure 6:
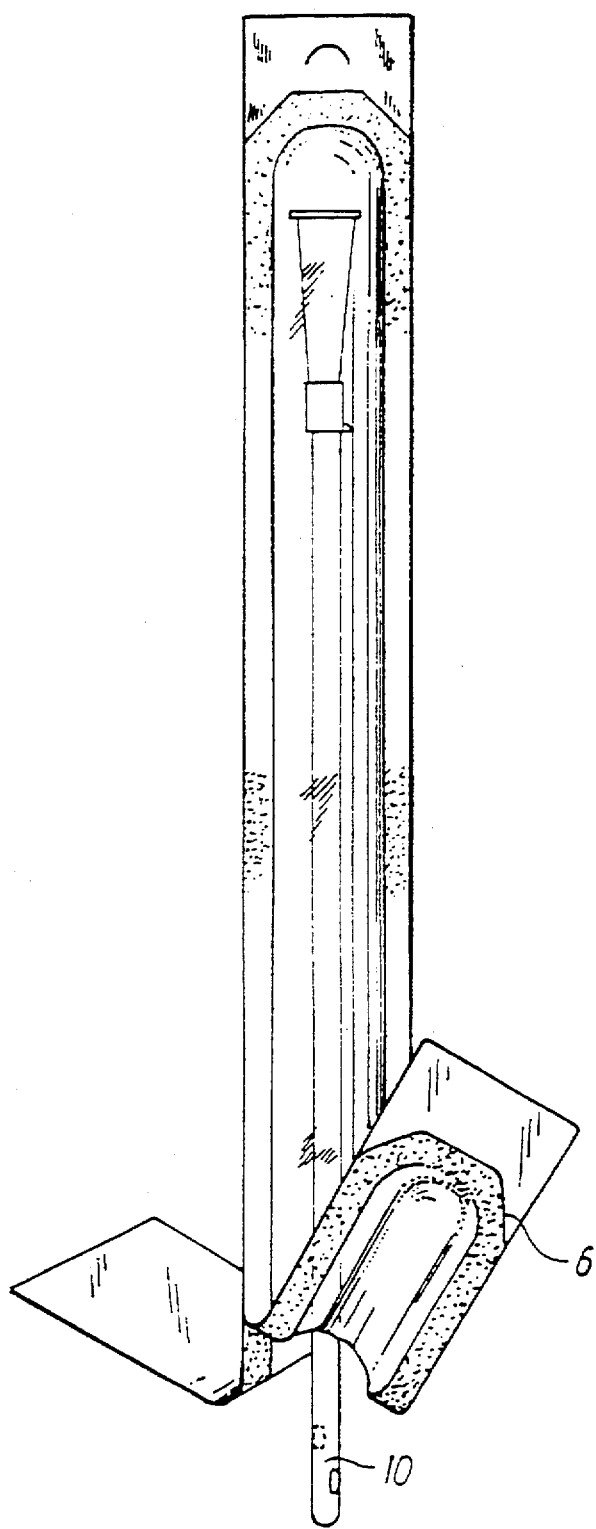

The invention will in the following be explained in more detail and with reference to the schematical drawing where FIGS. 1–3 show an embodiment of an applicator according to the invention seen in a plane view, a longitudinal section and a cross section along the line III—III in FIG. 2, respectively, whereas, FIGS. 4–6 illustrate the use of the applicator in connection with application of a catheter.

In the embodiment in FIGS. 1–3, the applicator according to the invention is designed as an elongated packaging sheath composed of two foil blanks which in the shown embodiment comprise a front wall 1 in the form of a transparent single-layer plastic foil eg. of polyethylene, and a rear wall 2 designed as a laminate of a plastic foil layer 2a, eg. of polyethylene, joined with the front wall, and a back layer 2b joined with the opposite side of the plastic foil layer and which as explained in the following may be of a gas-permeable paper type which is suitable for medical employment.

The foil blanks may, however, also consist of other suitable foil materials in the form of single-layer foils or laminates of plastic, metallic foils and/or paper.

The front wall 1 and the rear wall 2 are both at the side edges and at the ends of the sheath joined in peeling zones 3–6, of which the peeling zones 3 and 4 along the side edges of the sheath are linear and reach all the way to the respective edges of the front wall 1 and the rear wall 2 whereas the peeling zones 5 and 6 at the ends of the sheath may, as shown, have a curved or bent course and are drawn somewhat back from the end edges of the front wall 1 and the rear wall 2 such that outside these peeling zones 5 and 6 there are non-joined end portions 7 and 8, respectively, of the foil walls 1 and 2.

In the thus designed packaging sheath, a medical catheter 9 for insertion into a body canal, eg. a urethra catheter, is placed with its distal insertion end 10 opposite the peeling zone 6 at the lower end of the packaging sheath, this peeling zone forming a first zone of the edge joint formed in the peeling zones.

In the shown embodiment, the packaging sheath and the edge joints are furthermore, as shown in FIG. 3, designed in such a way that the front wall 1 encloses the catheter 9, 10 relatively closely in its full length. However, this design may not be considered as limitative for the invention as there is nothing to prevent the applicator packaging from being designed with a less elongated, eg. almost square, surface shape which may be appropriate for receiving catheters of larger lengths when bending or rolling up the catheter and with its distal insertion end situated eg. opposite a corner zone of the edge joint.

When packing catheters of the stated kind, the single-layer plastic foil serving as a front wall 1 for the applicator is advanced as a wide foil breadth where a number of cavities are formed in each of which there is placed a catheter 9, 10. This foil breadth is subsequently joined with the laminate serving as a rear wall 2 for the applicator along the entire circumference of each cavity.

The applicators may then be provided with hanging devices outside the edge joint, eg. in the form of a hole 12 through the front wall 1 and/or an adhesive tape 13 provided with a protective layer and placed on the rear wall 2.

The catheters can now be sterilized, eg. by gas sterilization through the gas-permeable back layer 2a and eg. slotted apertures 15, which are placed within this layer, in the foil layer 2b of the rear wall laminate. These apertures are placed within the edge joint but preferably in the proximity of the peeling zone 5 serving as second zone of the edge join in order to avoid contact between the paper layer 2b and the part of the catheter 9 meant for insertion into the urethra.

As the applicator in the shown embodiment is meant for urethra catheters of the kind provided with a friction-reducing surface coating which is activated by moistening with water immediately prior to the insertion of the catheter, the applicator is designed such that this moistening may be carried out while the catheter is in the packaging by an initial separation of the front wall 1 and the rear wall 2 of the sheath either at the lowest peeling zone 6 or the top peeling zone 5 defining a second zone of the edge joint which is remote in relation to the above-mentioned first zone 6 serving as initial separation zone for the separation of the catheter from the packaging in connection with the insertion.

As shown in FIG. 5, there may through the aperture formed by separation of the front wall 1 and the rear wall 2 at the peeling zone be poured a moistening fluid, eg. distilled water, in and out again to be used in the preparation of the catheter which typically takes about 30 seconds.

For this preparation the packaging sheath is preferably provided with instructions for the initial separation of the sheath walls 1 and 2 in connection with the moistening, eg. in the form of a relatively simple graphic instructions 14 on the outside of the rear wall 2 as shown in FIG. 4.

Subsequent to the preparation and the pouring out of the used water Quantity from the catheter space 11, the catheter 9 may be taken out from the packaging through the aperture at the peeling zone 5 whereby access is achieved for gripping the proximal coupling part 16 of the catheter, which is designed in a known way for coupling with a hose assembly. According to the invention, the application of the catheter is, however, effected in a more advantageous, contamination-free way by touching only the applicator through initial separation of the sheath walls. 1 and 2 at the peeling zone 6 which forms the first zone of the edge joint. As soon as the distal insertion end 10 of the catheter 9 is exposed, the insertion into the urethra may begin and under continuous pull in the now separated sheath walls 1 and 2 perpendicular to the longitudinal direction of the catheter, there is effected a gradual, complete separation of these walls whereby at the same time, the catheter is introduced into the urethra with no touching.

The method and the applicator according to the invention is not restricted to use in connection with a catheter of the kind which requires moistening prior to the application, but may to the same extent be used with a catheter which is packed in a ready-for-insertion state.

I claim:

1. The combination of a medical catheter for insertion into a body canal, in particular a urethra catheter, and of the kind provided with a friction-reducing surface coating, and a packaging composed of two essentially rectangular foil blanks (1,2) forming walls for a catheter space (11) and joined to each other by an edge joint extending along all side edges of the foil walls (1,2) and composed of essentially linear peeling zones (3–6) permitting complete separation of the two foil walls (1,2), said edge joint including a predetermined first end zone (6) outside which end portions (8) of the foil walls are not joined, characterized in that the catheter (9) is positioned in said catheter space (11) with its distal insertion and (10) opposite said predetermined first and zone (6) of the edge joint to enable said packaging to be used as an applicator for contamination-free application of the catheter (9) through gradual, complete separation of the foil walls (1,2) in said peeling zones (3–6) in the direction away from said first zone (6) by a pull essentially perpendicular to the longitudinal direction of the catheter with concurrent removal of the catheter from the catheter space for insertion of the catheter (9) into said body canal without touching the catheter.

2. The combination claimed in claim 1, characterized in that also and portions (7) of the foil walls (1,2) outside a second end zone (5) of the edge joint remote from said first zone are not joined to each other.

3. The combination claimed in claim 1 in which the catheter is of the kind where the friction-reducing surface coating is activated by moistening, characterized in that the packaging is provided with instructions (14) for initial separation of local parts of the two walls (1,2) merely at said first and zone or said second end zone of the edge joint in order to permit preparation of the catheter (9) by introduction and removal of a moistening medium through the thus formed aperture prior to said application of the catheter.

4. The combination claimed in claim 2, in which said foil walls (1,2) comprise a front wall and a rear wall of which the front wall (1) is a transparent single-layer plastic foil, whereas the rear wall (2) comprises a laminate composed of a plastic foil layer (2a) joined with the front wall and of back layer (2b) joined with the opposite side of the plastic foil layer, characterized in that said instructions (14) are positioned on the backside of said back layer (2b).

5. The combination claimed in claim 4, characterized in that said back layer (2b) is of gas-permeable paper.

6. The combination claimed in claim 5, characterized in that the plastic foil layer (2a) of the rear wall (2) is provided, within the edge joint, with at least one aperture (15) for use with gas sterilization of the catheter (9) after its positioning in said packaging.

7. The combination claimed in claim 6, characterized in that said aperture (15) is provided in the proximity of said second zone (5).

8. A method for producing the combination as claimed in claim 1, in which the packaging is formed by joining two essentially rectangular, edge-joined foil blanks (1,2) in essentially linear peeling zones extending along their edges to provide a catheter space (11) defined by said edge joint, whereby end portions (7, 8) of the foil blanks outside a predetermined first end zone (6) of said edge joint are not joined, characterized in that prior to completion of said edge joint the catheter (9) is positioned between said foil blanks (1, 2) with such an orientation that its distal insertion and (10) will be positioned opposite said predetermined first end zone (6) of the edge joint.

9. The method chimed in claim 8, characterized in that the catheter (9) is sterilized after completion of the edge joint by a gas-sterilization through said back layer (2b) and said aperture (15) in the single-layer plastic foil (2a) of the rear wall of the packaging.

10. A method for removal of a medical catheter, characterized in that initial opening of the packaging is effected by means of said non-joined end portions (4,8) of said fail walls. (1,2) followed by gradual, complete separation of said walls (1,2) in said peeling zones (3–6) in the direction away from said predetermined first end zone (6) by a pull essentially perpendicular to the longitudinal direction of the catheter and concurrent removal of the catheter.

11. The method claimed in claim 10 for use with the combination of any of claims 3 to 7, characterized in that prior to removal of the catheter a preparation of the catheter (9) is effected by initial separation of local parts of the foil walls (1,2) merely at said predetermined first end zone (6) or said second end zone (5) of the edge joint and introduction and removal of a moistening medium through the aperture provided by said initial separation.

12. The method claimed in claim 10, characterized by its use for direct insertion of the catheter into a body canal, in particular the urethra, concurrent with said removal using said packaging as an applicator for said insertion.

* * * * *